United States Patent [19]
Chin et al.

[11] Patent Number: 6,149,889
[45] Date of Patent: Nov. 21, 2000

[54] RADIOACTIVE PARTICLES AND METHODS FOR PREPARING SAME

[75] Inventors: Tsung-Shune Chin; Fong-In Chou, both of Hsinchu; Wing-Yiu Lui, Taipei, all of Taiwan

[73] Assignee: Department of Health The Executive Yuan, Taipei, Switzerland

[21] Appl. No.: 09/116,795

[22] Filed: Jul. 16, 1998

[30] Foreign Application Priority Data

Mar. 12, 1998 [TW] Taiwan .................................. 87103631

[51] Int. Cl.[7] ........................... A61K 51/00; A61M 36/14
[52] U.S. Cl. ........................ 424/1.61; 424/1.77; 424/1.11; 424/1.37; 501/87; 501/1; 501/11; 501/80; 264/641
[58] Field of Search ................................... 424/1.11, 1.37, 424/1.61, 1.65, 1.29, 1.81, 1.77; 264/669, 641, 11; 501/1, 87, 80, 96.1; 425/253

[56] References Cited

U.S. PATENT DOCUMENTS

| | | | |
|---|---|---|---|
| 4,789,501 | 12/1988 | Day et al. ................................. | 252/645 |
| 5,011,677 | 4/1991 | Day et al. ................................ | 424/1.11 |
| 5,011,797 | 4/1991 | Day et al. ................................. | 501/33 |
| 5,302,369 | 4/1994 | Day et al. ................................ | 424/1.29 |
| 5,762,950 | 6/1998 | Yli-Urpo et al. ........................ | 424/422 |
| 5,885,547 | 3/1999 | Gray ........................................ | 424/1.37 |

*Primary Examiner*—Jose' G. Dees
*Assistant Examiner*—Dameron Jones
*Attorney, Agent, or Firm*—Harness, Dickey & Pierce, P.L.C.

[57] ABSTRACT

A nuclear medical drug for localize radiotheraphy of a tumor and methods for its preparation. The drug includes a radioactive ceramic or glass particle having biocompatiblity. Ceramic or glass particles prepared by traditional processes become radioactive particles with pure β-particle-emitting radionuclides after being irradiated with an appropriate flux of neutrons. The radioactive particle with suitable particle size can then be dispersed into a contrast medium for injection or can be implanted by operation.

18 Claims, 6 Drawing Sheets

(2 of 6 Drawing Sheet(s) Filed in Color)

圖5、添加粒徑74μm之DCP粒體後,人類肝癌細胞之生長情形

Figure 5 shows the growth of the hepatoma after DCP particles of 74μm are added to hepatoma cells cultures.

圖6、活體肝癌注射放射性陶瓷粒體前（A）、後（B）之比較
Figure 6 shows a comparison of the liver cancer before (Figure 6A) and after (Figure 6B) the radioactive ceramic particles are injected.

RADIOACTIVE PARTICLES AND METHODS FOR PREPARING SAME

FIELD OF THE INVENTION

The present invention relates to an inorganic nuclear medical composition for use in the localized radiotherapy of a tumor. More particularly, the present invention relates to a nuclear medical composition appropriate for such use which comprises bio-active or bio-inert ceramic or glass particles with pure β-particle-emitting radionuclides.

BACKGROUND OF THE INVENTION

When tumor growth is recognized in the body, excision of the tumor mass by surgery is regarded as the therapy of choice. However, this approach, while producing very satisfactory results as a general measure, is effective only for patients with tumors at an early stage of development. For example, in the case of late-stage primary liver cancer having underlying cirrhosis (common in Africa and in some Asian countries), the prognosis for surgical excision or resection is relatively poor. Regardless of the developmental stage of the cancerous mass, therapy through excision is frequently undesirable due to the possibility of missing related growths metastasized to a remote site, the physical scarring left by frequently radical surgical technique, and the risks commonly associated with surgery of any type.

Therefore, it is desirable to develop an effective therapy for cancer at all stages of development. The high radiation dosages required for traditional radiotherapy usually results in cellular damage to normal tissue adjacent the tumor. Moreover, the high radiation dosage invariably inhibits the normal immunological functions of the cancer patient and causes other irreparable damage. Hence, while radiotherapy has its advantageous applications, it is not ideal. A preferred therapy is one that would involve the use of tumorphilic substances with radionuclides in which the substances accumulate in the tumor tissue by intravasation or by direct implantation into the tumor tissue. This approach provides more specific high radiation dosage at the tumor sites.

SUMMARY OF THIS INVENTION

One undesirable result of traditional radiotherapy for cancer is that the requisite high radiation dosage usually results in cell damage of normal tissue. The present invention discloses neutron-activated ceramic or glass particles for localized radiotherapy of a tumor and the methods for preparing the same, which concentrates a more specific high radiation dosage on the tumor or cancer at the site itself and which minimizes damage to normal tissue. Moreover, the nuclear medical composition of the present invention is more stable than isotopes used in conventional radiotherapy and lasts longer in the tumor tissue, thereby providing extended residence time desirable to deliver the appropriate cancer-destroying dose.

The radioactive ceramic or glass particles of the present invention are inorganic substances primarily carrying β-particle (e.g., $^{32}P$) emitting radionuclides. The radioactive ceramic or glass particles can be suspended in iodized oil (iodoinated ester of poppy seed oil or lipiodol) and injected into the tumor tissue by intravenous administration or through surgical implantation, thus exposing the tumor cell to a higher radiation dosage and thereby leading to more effective destruction of the tumor cells. By focusing administration directly to the site, the nuclear medical composition of the present invention can minimize the cell damage of the normal tissue adjacent to the tumor and effectively overcome drawbacks of the traditional radiotherapy or chemotherapy for cancer patients.

The features and advantages of the present invention will be apparent from the following detailed description with reference to the accompanying drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 6 shows a comparison of the liver cancer before (FIG. 6A) and after (FIG. 6B) the radioactive ceramic particles are injected.

DETAILED DESCRIPTION OF THE PRESENT INVENTION

The present invention is characterized by use of neutron-activated ceramic particles (including glass) which become pure β-particle-emitting substances after neutron activation. The particles become radioactive after being bombarded with a suitable flux of neutrons in a pneumatic tube provided in association with the nuclear reactant.

To be effective emitters, the selected ceramic particles must possess the following properties:

(1) First, the particles must be biocompatible, such as calcium phosphate-based biomedical ceramics or glass.

(2) Second, the particles must quantitatively comprise enough elements so as to be readily activated by neutrons to become a radiation-emitted radionuclide with an appropriate half-life. The elements of the particles must have enough neutron-capture cross-section to produce β-particle-based radionuclides. The β-particles have high energy and an appropriate penetration distance, which are capable of releasing their entire energy complement within the tumor tissue to effectively kill the cancer cells and to minimize damage to adjacent normal cells or to attending medical personnel. The level of radiation activity of the neutron-activated ceramic or glass is selected and fixed based upon the need for therapy given the particular cancer involved and its level of advancement. The ideal half-life of the radionuclides is somewhere between days and months. On the one hand, it is impractical to treat tumors with radionuclides having too short a half-life, this characteristic limiting therapy efficiency. On the other hand, in radiotherapy it is generally difficult to trace and control radionuclides having a long half-life. If the particles are generated from fusion or decay from other nuclides instead of their being obtained from neutron activation, care and handling become problems, hence the neutron activation and consequent considerations of radiation safety further compromise the practical advantages of this approach to therapy. Therefore, materials that can become β-particle-emitting radionuclides after being irradiated with neutrons are particularly preferential for use in localized radiotherapy of tumors.

(3) Third, the particles must be of a suitable size. The size of the particles for treatment depends upon such variables as the surface area of the tumor, capillary permeability, and the selected method of introduction into the tumor (i.v. versus implant by surgical operation). The size of the particles suspended in the formula for i.v. ranges from a few $\mu$m to tens of $\mu$m while that for surgical implant tens of $\mu$m to tens of mm.

(4) Fourth, some ceramic processes involve inclusion of extraneous substances as contaminants which might produce undesired radionuclides. Should these be well taken care of, the size of the particles can then be controlled by granulation and meshing.

There are many processes for producing small granular ceramic or glass particles. One of these involves the introduction of small amounts of the ceramic particles passind through a high-temperature melting region. Ceramic spherules are yielded by surface tension during melting. After the solidification, condensation, collection and sorting processes, ceramic spherules of various sizes can be obtained. The particle size of ceramic spheroid can be controlled by the mass of granules introduced into the high-temperature melting region or can be controlled by collecting spheroids of various sizes through the selection of sedimentary time during liquid-sedimentation.

The present invention is characterized by ceramic or glass particles which can become β-particle-emitting radionuclides for localized radiotherapy of a tumor or cancer after neutron-activation. Hence the ceramic or glass materials for preparing those particles can be obtained commercially or from ultra-pure ceramic raw materials if the commercial products do not meet specifications for one reason or another. The ceramic or glass particles for radiation exposure in this invention can be yielded by traditional ceramic processes, which are well known by those skilled in this art. The ceramic processes such as solid state reaction, chemical co-precipitation, sol-gel, hydrothermal synthesis, glass melting, granulation, and spray pyrolysis can be applied in this invention for the production of specific particles.

The ceramic or glass particles of suitable size which are obtained commercially or which are produced by the processes described above are washed twice with distilled water. Then the supernate is decanted after sedimentation for 3 minutes. The above two steps are repeated 3 times to remove the micro-granules adhering on the surfaces of the particles. Then a certain amount of ceramic or glass particles prepared from the processes described above are introduced into a quartz tube. After being sealed, the quartz tube is placed inside a plastic irradiation tube, then the irradiation tube is closed. The irradiation tube is put into a vertical tube of the nuclear reactor and the multiple tube assembly is irradiated with an approximated neutron flux (e.g., equal to $5\times10^{11}$ n/cm$^2$-sec$^1$ or above $5\times10^{11}$ n/cm$^2$-sec$^1$; preferentially equal to $1\times10^{12}$ n/cm$^2$-sec$^1$ or above $1\times10^{12}$ n/cm$^2$-sec$^1$) for an approximated exposed period (e.g., 24~30 hours). Following exposure, the irradiation tube is taken out of the nuclear reactor for cooling. According to this method, ceramic or glass particles carrying pure β-particle radionuclides can be generated.

Exemplary Method of Determining Radiation Activity:

Analyses for the radiation activity of the ceramic or glass particles of this invention are described as follows. One hundred mg of radioactive ceramic or glass particles were mixed with 1.0 ml of concentrated HCl to form a solution of radioactive ceramic or glass. Then 0.1 ml of this solution was diluted 10-fold. Subsequently, a certain amount of dilute solution was dropped into a radiation-counting cell, then the activity of β-particles was counted after the dilute solution in the radiation-counting cell became dry. The activity of β-particles was detected by measuring the counting efficiency at the site, which was 2.0 cm below the standard emitting source. Then the counting efficiency was inversed into the activity ($\mu$Ci) of the detecting sample. If the ceramic or glass particles are insoluble in concentrated HCl, the particles should be well mixed with a suitable solvent to make a suspension containing insoluble ceramic or glass particles. The suspension was quickly sampled in order to detect γ rays. The method for γ ray detection described above was carried out by counting 10.0 ml of dilute sample in a sealed detecting glass bottle of a multiple-channel energy spectrum analyzer (e.g., multiple-energy spectrum analyzer of the Canberra series) by a high efficiency germanium detector (e.g., HP Ge Detector System). The detection efficiency of the detector for various γ rays was calibrated by the efficiency of 7 energy peaks of Eu-152. The radiation activity of each activated radionuclide was measured by the ratio of counting value per minute (CPM) versus counting efficiency. The radiation activity is represented as $\mu$Ci.

The ceramic or glass particles of present invention disclosed herein are characterized by:

(1) First, the major radioactive radionuclide of the ceramic or glass particles is $^{32}$P, which is a pure β-particle-releasing radionuclide with a maximum energy of about 1.709 MeV. The radionuclide has a high linear energy transferring efficiency, wherein the half-life of the radionuclide is about 14.2 days. The radioactive particles are preferred for localized radiotherapy of a tumor or cancer.

(2) Second, the stability of the radioactive ceramic or glass particles in the serum is high, and the particles have high affinity to human tumor or cancer cells (e.g., hepatoma).

(3) Third, there is no dependent relationship between radiation activity of the ceramic or glass particles and their sizes. The preferred ratio of calcium/phosphorous (Ca/P) in the composition of various ceramic or glass particles is about 2~0.5 by controlling approximate radiation time and neutron flux. Preferentially, the ratio of calcium/phosphorous (Ca/P) in the composition of various ceramic or glass particles is about 1.8~0.6. Therefore, the sizes of the radioactive ceramic or glass particles can be well controlled by selecting various composites.

PREFERRED EMBODIMENTS

Example 1

Calcium Phosphate Glass Particles

Granulation and Meshing

Three glasses such as DCP (dicalcium phosphate with a formula 2CaO.P$_2$O$_5$ or Ca$_2$P$_2$O$_5$), CaO-33 (an eutectic calcium phosphate composition comprising 33 weight by parts of CaO), and CaO-47 (an eutectic calcium phosphate composition comprising 47 weight by parts of CaO), with a Ca/P ratio value between 1.25~0.5 were produced. The compositions of these three glasses are shown in Table 1.

TABLE 1

Composition of the glass per 100 g

| Glass/material | CaHPO$_4$ 2H$_2$O | Ca(H$_2$PO$_4$)$_2$ H$_2$O | CaCO$_3$ | Ca/P |
|---|---|---|---|---|
| DCP | 100.0 g | — | — | 1 |
| CaO-33* | 30.88 g | 69.11 g | — | 0.625 |
| CaO-47* | 93.56 g | — | 6.64 g | 1.124 |

*CaO-33 represents an eutectic calcium phosphate composition containing 33 weight by parts of CaO;
CaO-47 represents an eutectic calcium phosphate composition containing 47 weight by parts of CaO According to the composition shown in Table 1, certain amounts of high purity of the CaHPO$_4$.2H$_2$O, Ca(H$_2$PO$_4$)$_2$.2H$_2$O and Ca(OH)$_2$ powder were independently mixed with approximate amount of ethanol and 2-fold weight of the aluminum oxide (Al$_2$O$_3$) balls, then the mixtures were milled with a ball miller for 1~3 days. Subsequently, the granulated products were dried by infrared heating. The dried powders were placed in a platinum crucible and were heated for 2 hours to a constant temperature that was 50~100° C. higher than the melting point of the powders (about 1050~1300° C.). The melting glass in the crucible was introduced into water for fast cooling, thereby producing an amorphous glass. The X-ray diffraction analysis indicates that no crystallized phases in DCP or CaO-33 glasses were yielded after fast cooling, and the spectra of X-ray diffraction shows a broad diffraction peak, which indicates that the phase of products was glass in all cases. However, there was still a crystallized phase, such as β-Ca$_3$(PO$_4$)$_2$ and β-Ca$_2$P$_2$O$_7$, present in CaO-47 after fast cooling, caused by a deficiency of P$_2$O$_5$. In fact, P$_2$O$_5$ plays a role as glass former herein. Too small an amount of P$_2$O$_5$ in the glass will reduce the glass forming ability, causing crystallization and devitrification to be present in or on the surface of the glass during fast cooling process. If the ceramic phase is preferred over the glass phase, the glass produced by the above process can be placed in a high temperature oven to carry out a crystallized thermal treatment at a temperature higher than its crystallization temperature (about 400~800° C.). The ceramic or glass products were granulated subsequently with a planetary ball miller, then the glass or ceramic particles consisting of calcium phosphate with sizes of 35 μm to 40 μm were sifted out by using a No. 325 mesh. The particles selected through sifting were washed with water to remove the micro-granules absorbing on the surfaces. Finally, the shapes and the sizes of yielded particles were analyzed respectively by a scanning electron microscope (SEM) and a laser scattering particle-size analyzer.

According to the composition shown in Table 1, Ca(OH)$_2$ of high purity was mixed with concentrated phosphoric acid (H$_3$PO$_4$) to form a solution, and the Ca/P ratio was adjusted to satisfy Table 1. Then the mixture was sprayed or nebulized by a ultrasonic nebulizer to yield particles with a size on the order of μm into a heated furnace. The water within the μm-sized particles was dried in a high temperature zone, then the oxides of calcium and phosphorous were melted to form granules at 1000° C. to 1200° C. Composition of the particles could be controlled by the concentration of the solution at the beginning. Observation with a SEM indicated that shape of the particles were spherical with a diameter of 0.1~5 μm.

Spray Pyrolysis

The DCP solution made of Ca(OH)$_2$ and concentrated phosphoric acid as mentioned above could also be sprayed or nebulized by an ultrasonic nebulizer into a high temperature phase, which is typically an oxygen-acetylene based high-temperature flame, and the glass was melted after the water was evaporated. The DCP glass subsequently becomes spherical because of the surface tension. Then the spherules were conveyed into an oven of 700° C. by the flow of flame. The spherical shape remained after cooling. Observation with a SEM indicated that the obtained products were spherical granules with diameters of 0.1~5 μm.

Neutron Exposure and the Determination of the Radiation Activity

The spherical granules generated according to the previous processes could be activated by the methods of neutron activation described in the detailed description of the present invention. In order to understand the composition of the contaminants in materials, Ca(OH)$_2$ and Ca(H$_2$PO$_4$).H$_2$O obtained commercially were bombarded with neutrons, then the radiation activity was subsequently determined. The elements in the materials will become a γ ray or β-particle-emitting radionuclide after being bombarded with neutrons. The nuclear reaction formulas of various elements activated with neutron are shown in Table 2. Column 1 is the nuclear reaction formula; Column 2 is the half-life of produced radionuclide; Column 3 is the percentage of various elements present in nature; Column 4 is the probability of neutron absorption, that is, the cross section of neutron capture, wherein the unit is a barm; Column 5 is the γ energy (keV) and strength percentage used in detection.

TABLE 2

| Nuclear reaction | Half-life | Percentage of isotope present in nature (%) | Neutron capture cross section | Major energy (keV) and intensity (%) of γ ray |
|---|---|---|---|---|
| $^{31}$P(n, γ)$^{32}$P | 14.2 d | 100 | 0.19 | No γ |
| $^{46}$Ca(n, γ)$^{47}$Ca | 4.73 d | 0.0033 | 0.25 | 1296(77) |
| $^{48}$Ca(n, γ)$^{49}$Ca | 8.80 min. | (0.185) | 1.1 | — |
| $^{47}$Ca → $^{47}$Sc | 3.40 d | — | — | 160(74) |
| $^{45}$Sc(n, γ)$^{46}$Sc | 84.0 d | 100 | 23 | 889(100) |
| $^{152}$Sm(n, γ)$^{153}$Sm | 46.2 hr | 26.6 | 210 | 100(37) |
| $^{50}$Cr(n, γ)$^{51}$Cr | 27.8 d | 4.3 | 15.9 | 320(10.2) |
| $^{58}$Fe(n, γ)$^{51}$Cr | 45.0 d | 0.33 | 1.2 | 1098(56) |

* The nuclides were produced according to the nuclear reaction, all other nuclides the remainder described above. Except of $^{51}$Cr was produced by electron capture, all other remainder nuclides, $^{32}$P, $^{47}$Ca, $^{49}$Ca, $^{47}$Sc, $^{46}$Sc, $^{153}$Sm, and $^{59}$Fe, were undergone β-decay.

Figure 1:
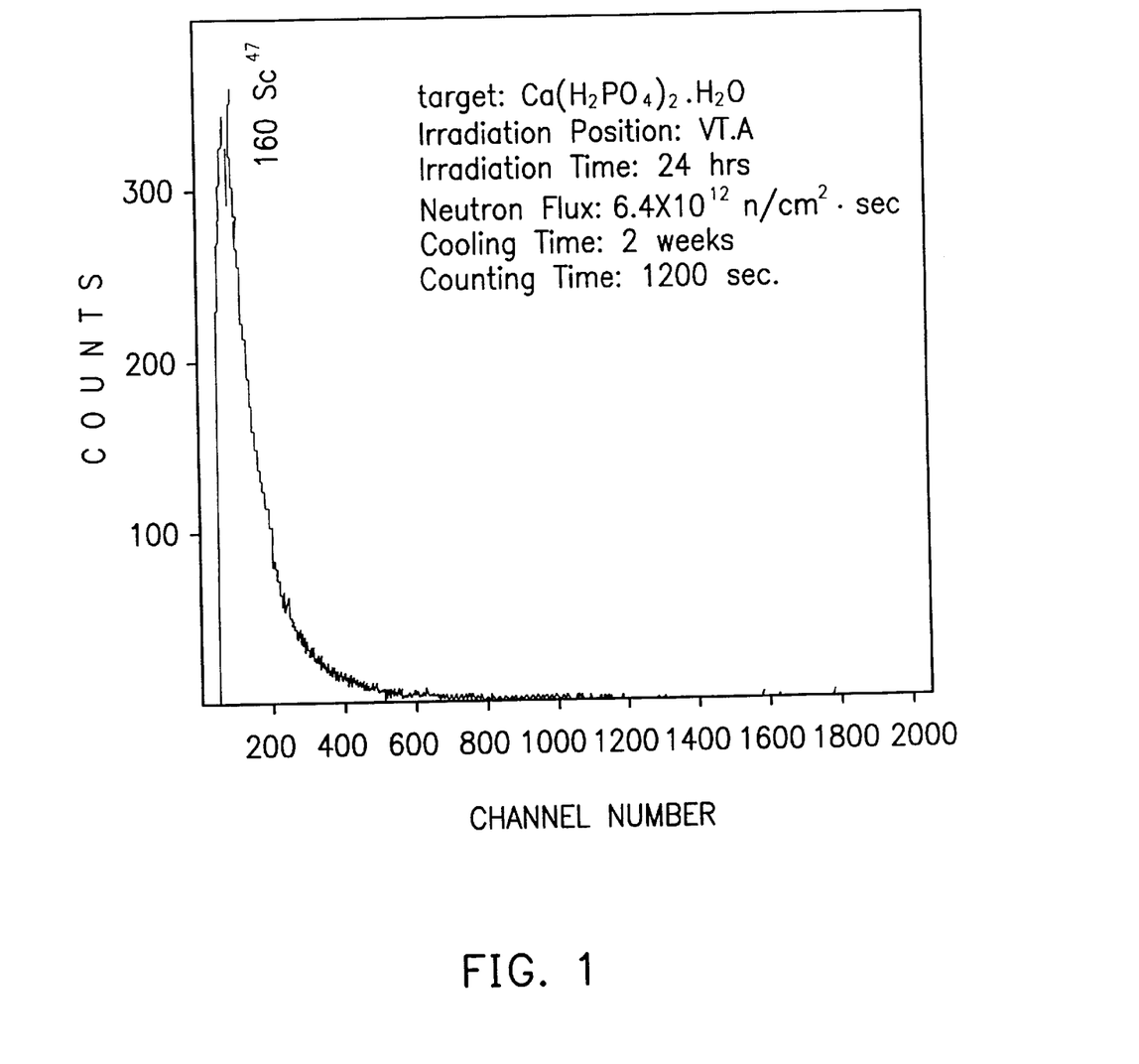
FIG. 1 shows the γ-energy spectrum of $Ca(H_2PO_4)_2 \cdot H_2O$ after irradiation with neutrons.
Figure 2:
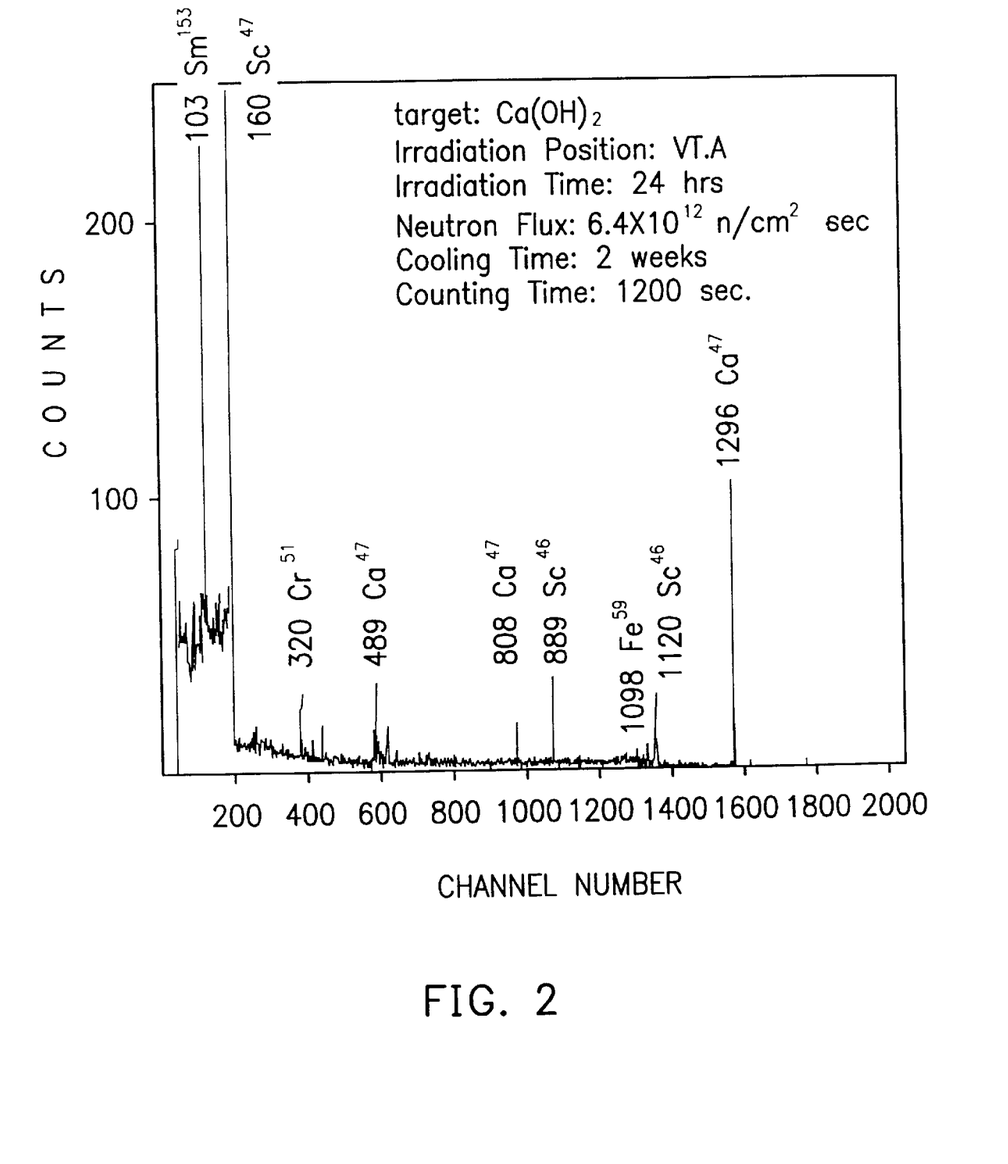
FIG. 2 shows the γ-energy spectrum of $Ca(OH)_2$ after irradiation with neutrons.

FIG. 1 and FIG. 2 represent independently the γ energy spectrum of Ca(H$_2$PO$_4$)$_2$.H$_2$O and Ca(OH)$_2$ after neutron activation. Ca(H$_2$PO$_4$)$_2$.H$_2$O contains phosphate ion (PO$_4^-$ 3) which will become a $^{32}$P nuclide after neutron activation. The β-particles emitted by the $^{32}$P will result in continuous spectra in the low energy region. The neutron-activated products are $^{47}$Ca and $^{47}$Sc. Hence, the results indicate that the major radiation released by the neutron activated Ca(H$_2$PO$_4$)$_2$.H$_2$O is β-particles. In addition, the γ energy spectrum of FIG. 2 indicates that the Ca(OH)$_2$ contains small amounts of $^{51}$Cr, $^{46}$Sc, and $^{59}$Fe, resulting from trace contaminants, e.g., Cr, Sc, and Fe. Table 3 shows the radiation activity of various nuclides obtained after two material powders being activated with neutron irradiation. The radiation activity is represented as μCi.

TABLE 3

| Target sample | Activity of nuclides (μCi) | | | | | | |
|---|---|---|---|---|---|---|---|
| | $^{32}$P | $^{47}$Ca | $^{47}$Sc | $^{46}$Sc | $^{153}$Sm | $^{51}$Cr | $^{59}$Fe |
| Ca(OH)$_2$ | — | 14.3 | 3.8 | 0.03 | 0.03 | 0.01 | 0.02 |
| Ca(H$_2$PO$_4$)$_2$ H$_2$O | 519 | 0.08 | 0.05 | — | — | — | — |

Note:
Neutron flux is about 6.4 × 10$^{12}$ n cm$^{-2}$ sec$^{-1}$
Irradiation site: Vertical radiation tube A (VT. A)
Irradiation duration: 24 hours The samples of glass particles (DCP, CaO-33, and CaO-47) with various sizes (1~20 μm and 20~40 μm) as well as tri-calcium phosphate (TCP) and hydroxylapatite (HA) were activated with neutron irradiation, and the radiation activity of each of the detectable radionuclides is shown in Table 4.

TABLE 4

| Target sample | Particle size | Activity of nuclides (μCi) | | | | | |
|---|---|---|---|---|---|---|---|
| | | $^{32}$P | $^{47}$Ca | $^{46}$Sc | $^{181}$Hf | $^{95}$Zr | $^{122}$Sb |
| DCP | 1~20 μm | 760 | 0.31 | 0.0004 | — | — | — |
| DCP | 20~40 μm | 780 | 0.31 | 0.003 | — | — | — |
| CaO33 | 1~20 μm | 960 | 0.24 | 0.0005 | — | — | — |
| CaO33 | 20~40 μm | 940 | 0.23 | 0.001 | — | — | — |
| CaO47 | 1~20 μm | 870 | 0.45 | 0.001 | — | — | — |
| CaO47 | 20~40 μm | 980 | 0.38 | 0.001 | — | — | — |
| TCP | 1~20 μm | 390 | 0.22 | 0.001 | — | — | — |
| TCP | 20~40 μm | 420 | 0.28 | 0.0007 | — | — | — |
| HA | 1~20 μm | 409 | 0.078 | 0.0002 | — | — | — |
| HA | 20~40 μm | 388 | 0.08 | 0.0006 | — | — | — |

Note:
Neutron flux is about 6.4 × 10$^{12}$ n.cm$^{-2}$.sec$^{-1}$
Irradiation site: vertical radiation tube A (VT. A)
Irradiation duration: HA is 24 hours; the others are 30 hours The results in Table 4 indicate that among the neutron-activated samples, the major activated radionuclides of DCP(1~20 μm, 20~40 μm), CaO-33(1~20 μm, 20~40 μm), and CaO-47(1~10 μm, 20~40 μm) are $^{32}$P, $^{47}$Ca, and $^{46}$Sc, wherein $^{32}$P is a pure β-particle-releasing radionuclide. The γ ray spectrums of the activated samples described above are shown as FIG. 3. The continuous spectrum in the low energy region results from the β-particles released by $^{32}$P.

Figure 3:
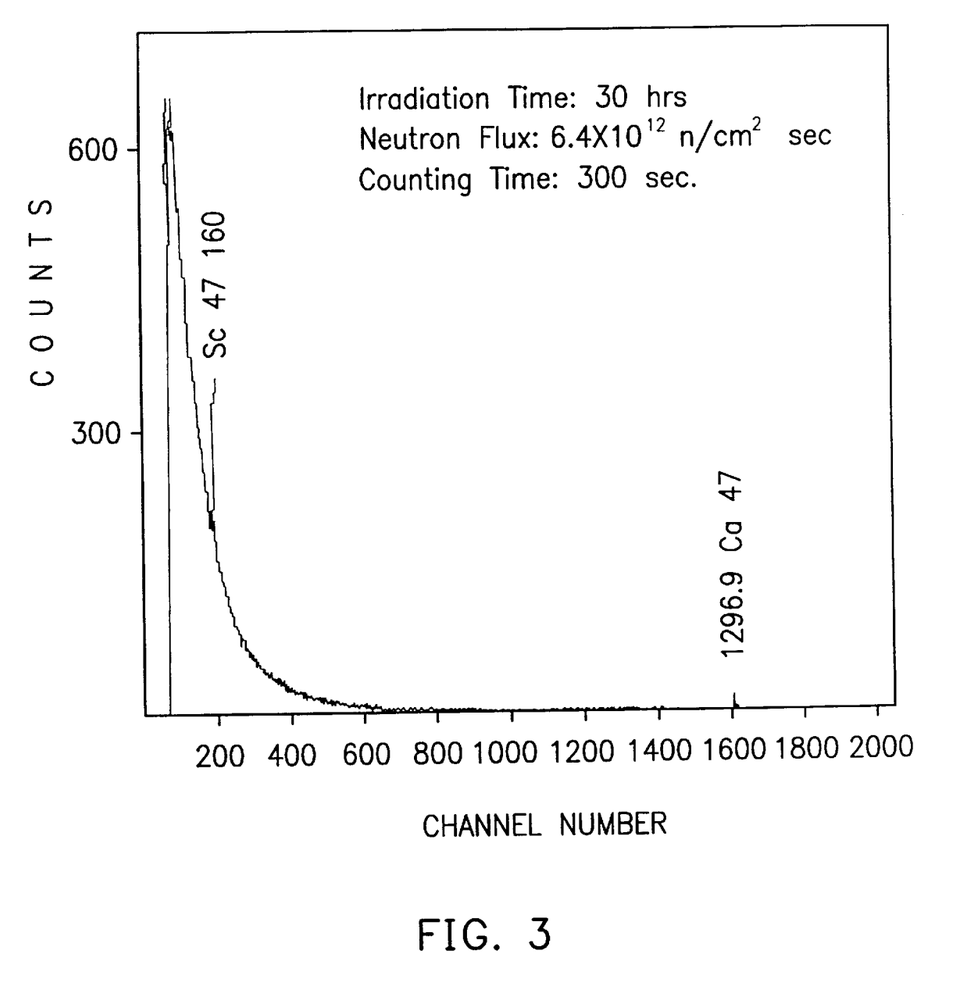
FIG. 3 shows the γ-energy spectrum of DCP(1~20 μm), DCP(30~40 μm), CaO-33(1~20 μm), CaO-33(30~40 μm), CaO-47(30~40 μm), TCP(1~20 μm), TCP(30~40 μm) after irradiation with neutrons.

Referring to FIG. 3, we can confirm that the major γ radionuclide is $^{47}$Ca.

Figure 4:
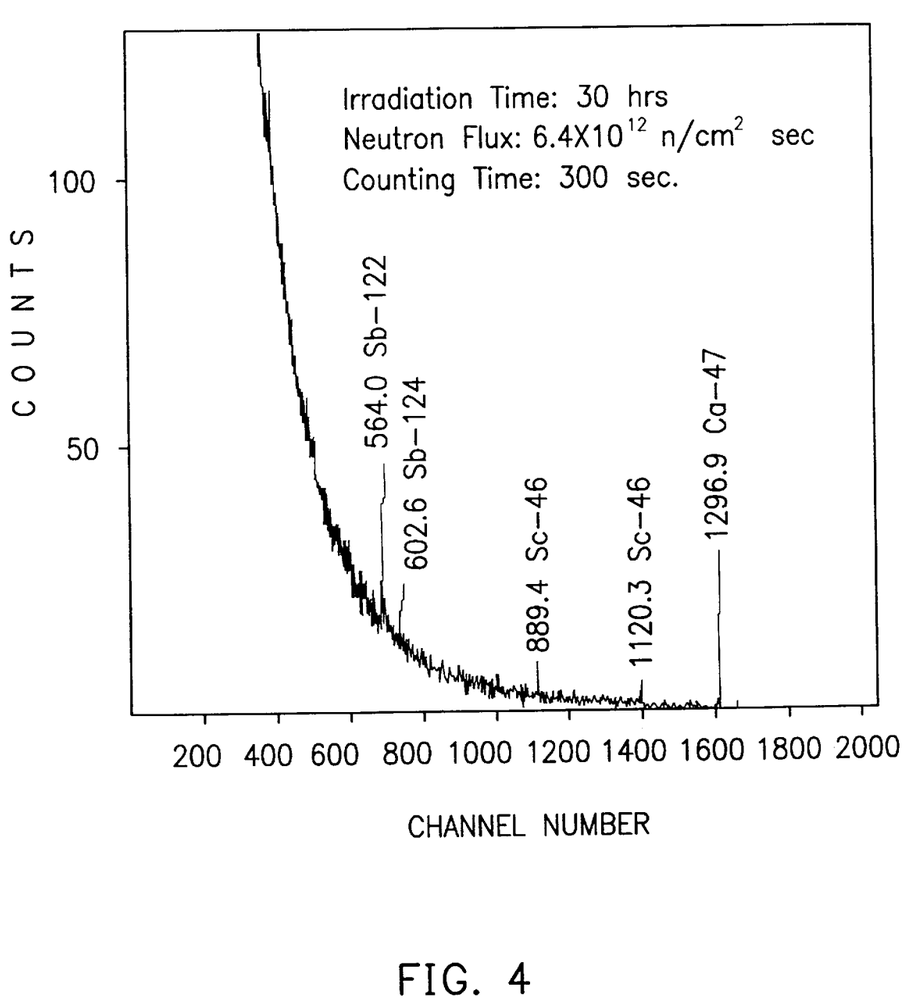
FIG. 4 is the partial magnified drawing of FIG. 3.

As shown in FIG. 4, another major radionuclide in this spectrum is $^{46}$Sc. The trace $^{46}$SC was produced by the trace contaminant, Sc. The trace $^{46}$Sc radionuclide is supposed to have no side-effect when used. Still referring to FIG. 4, the major radiation released by the neutron-activated powder are supposed to be β-particles.

The samples could be classified into three groups by size, including DCP (1~20 μm, 20~40 μm), CaO-33 (1~20 μm, 20~40 μm), and CaO-47 (1~10 μm, 20~40 μm), wherein the major activated radionuclides are $^{32}$P, $^{47}$Ca, and $^{46}$Sc, wherein $^{32}$P is a pure β-particle-releasing radionuclide. The specific activity of radiation and the type of radionuclides are not directly proportional to the size of yielded particles.

The major radionuclide and the radiation properties of the neutron-activated samples are shown in Table 5. The data in Table 5 indicate that the half-life of radionuclide is somewhere between days and deca-days. The energy and the strength of the β-particles emitted by the major radionuclide are quite high, and trace γ ray is present, which is harmless. Additionally, the present trace γ ray can provide a trace source for a γ-ray camera and the residual radiation dosage counted in the body in animal experiments, thus no extra γ ray emitted radionuclide is necessary as a supplement.

TABLE 5

The radiation activity of the major radionuclide in ceramic particles after neutron-activated

| Radionuclide | Half-life | Decay mode | Energy (MeV) and intensity (%) | Energy and strength of γ ray (Mev) | Percentage of internal conversion | Specific γ-ray emission | Nuclear reaction |
|---|---|---|---|---|---|---|---|
| $^{32}$P | 14.2d | β$^-$ | 1.71~100% | — | — | — | $^{31}$P(n, γ)$^{32}$P |
| | | | | | | | $^{32}$S(n, γ)$^{32}$P |
| $^{47}$Ca | 4.7d | β$^-$ | 0.66~83% | 0.48~6% | — | 5.7 | $^{46}$Ca(n, γ)$^{46}$Sc |
| | | | 1.94~17% | 0.83~6% | | | |
| | | | | 1.31~77% | | | |
| $^{46}$Sc | 84d | β$^-$ | 0.36~100% | 0.89~100% | — | 10.9 | $^{45}$Sc(n, γ)$^{46}$Hf |
| | | | 1.48~0.004% | 1.12~100% | | | |

TABLE 5-continued

The radiation activity of the major radionuclide in ceramic particles after neutron-activated

| Radionuclide | Half-life | Decay mode | Energy (MeV) and intensity (%) | Energy and strength of γ ray (Mev) | Percentage of internal conversion | Specific γ-ray emission | Nuclear reaction |
|---|---|---|---|---|---|---|---|
| $^{181}$Hf | 42.5 hs | $\beta^-$ | 0.40~4% | 0.133~40% | 46% | — | $^{180}$Hf(n, γ)$^{181}$Hf |
| | | | 0.41~92% | 0.136~6% | 9% | | |
| | | | others~4% | 0.17~2% | 2% | | |
| | | | | 0.346~13% | 1% | | |
| | | | | 0.476~2% | | | |
| | | | | 0.48~81% | 1% | | |
| $^{95}$Zr | 65d | $\beta^-$ | 0.36~43% | 1.73%~55% | | 4.1 | $^{94}$Zr(n, γ)$^{95}$Zr |
| | | | 0.40~55% | 0.76~43% | | | $^{94}$U(n, γ)$^{95}$Zr |
| | | | 0.88~2% | 0.23~0% through 90 hours $^{95m}$Nb | 2% | | |
| $^{122}$Sb | 2.74d | $\beta^-$ | 0.73~4% | 0.57~66% | — | 2.4 | $^{121}$Sb(n, γ)$^{122}$Sb |
| | | | 1.42~63% | 0.69~3% | | | |
| | | | 1.99~30% | 1.12~1% | | | |
| | | Electron capture | 3% | 1.26~1% | | | |

Example 2

Fabrication of Hydroxylapatite (HA) Particles by Granulation and Meshing

First, Ca(OH)$_2$ and Ca(H$_2$PO$_4$).H$_2$O powder were mixed to a molar ratio of 7:3, then the mixed powders were placed in a PVC bottle. In addition, some miller balls consisting of silicon carbide with the same weight as the mixed powders were added, and alcohol was added to serve as a mixing agent to generate a mixture. The mixture was then dried under an infrared lamp. The dried mixture was meshed subsequently with a 100-mm mesh. 50~100 g of the dry meshed mixture was placed in a cooking autoclave obtained on the market (e.g., Quanta, made in Italy), containing 80% by volume of de-ionized water. The autoclave was then heated to a thermo-equilibrium state by an electroheater with 800 W electric output to make a hydrothermal reaction at a high temperature. Particles of various sizes can be generated after cooking for 3~20 hours. After turning off the heating source, the products were meshed to select and sort after cooling, and washed twice with de-ionized water, then dried subsequently with an irradiation lamp.

The X-ray diffraction and SEM analyses of the products indicated that the crystallized hydroxyapatite was rod shaped with a length of 0.2 μm, and a diameter of 0.02 μm. The particles manufactured by this method were too small to use. Extra sintering and milling processes are needed for the above particles. The powders synthesized in the autoclave were placed into a mold and were molded by a press machine with a pressure of 100 MPa. Then the pressed pellets were placed in a high-temperature furance and heated to 1300° C. to sinter for 3 hours. Thereafter, the sintered HA was milled and meshed (if required) to obtain a HA powder of the desired size.

Neutron Irradiation and the Determination of Radiation Activity

The method of neutron activation was carried out according to the process described above in the Detailed Description. The major radionuclides and the energy of radionuclide are shown in Table 4 as HA being irradiated with neutrons for 24 hours. As shown in Table 4, the major activated radionuclides are $^{32}$P(388~409 μCi), $^{47}$Ca(trace), and $^{46}$Sc (very trace), wherein $^{32}$P is a pure β-emitting radionuclide.

Example 3

Manufacturing of Tri-Calcium Phosphate (TCP)

CaHPO$_4$.2H$_2$O and CaCO$_3$ powders were well mixed by granulation to a molar ratio of 2:1. After being dried, the dry mixed powders were put into an alumina crucible, then the crucible was heated to 1400° C. for solid state reaction for 2 hours. X-ray diffraction results indicated that the crystal phase of the particles were all α-TCP phase. Thereafter, the TCP ceramic particles were put into a planetary ball miller containing an appropriate amount of alcohol and ZrO$_2$ miller balls with 10 times the weight of the ceramic particles to grind for 1 to 3 days. Finally, the granulated products were dried with an infrared lamp and were sifted according to desired particle size.

The neutron activation was carried out according to the process described previously. The major radionuclides and the energy of the radionuclides are shown in Table 4 as TCP being irradiated with neutrons for 24 hours. As shown in Table 4, the major activated radionuclides of TCP (1~20 μm, 30~40 μm) are $^{32}$P (with an energy of 390~420 μCi), $^{47}$Ca (trace), and $^{46}$Sc (very trace), wherein $^{32}$P is a pure β-emitting radionuclide.

Example 4

As described previously, the generated ceramic or glass particles were sifted to select the particles of 35~40 μm, and were exposed to neutrons to obtain radioactive particles. The radioactive ceramic or glass particles were mixed with an appropriate contrast medium serving as a suspension (e.g., lipiodol or iodized oil) to form an injection medium containing radioactive ceramic particles.

Example 5

In Vivo Human Hepatoma and In Vivo Animal Test of the Radioactive Ceramic Particles In order to describe the therapeutic effects of the present radioactive ceramic particles for localized radiotherapy of tumors, human hepatoma cells and animals were used as testing materials herein.

Affinity Test Between HepG2 Cells and Biomedical Ceramic or Glass Particles

Figure 5:
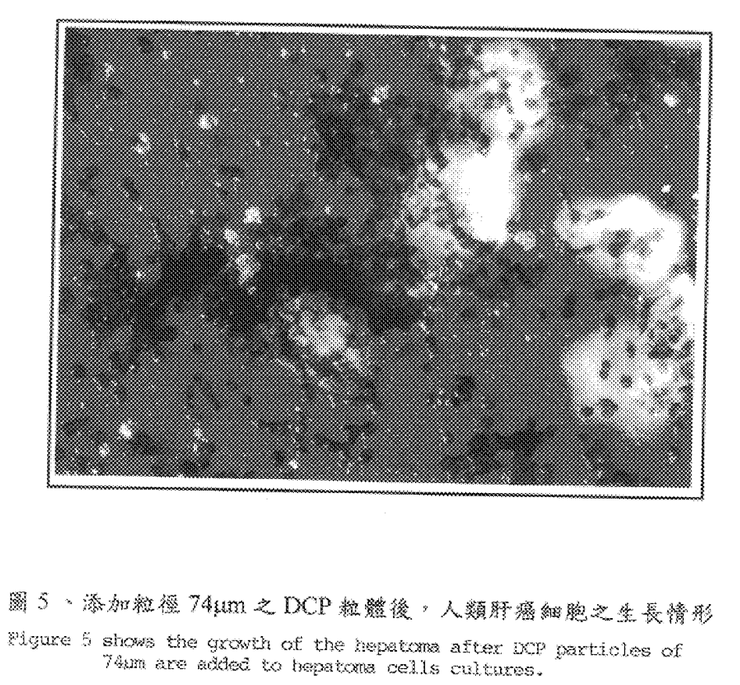
FIG. 5 shows the growth of the hepatoma after DCP particles of 74 μm are added to hepatoma cells cultures.

DCP ceramic particles sterilized by Co-60 radiation were added to a petri dish 70% full of HepG2 cells, and were cultivated in an incubator at a constant 37° C., 100% relative humidity, and 5% $CO_2$ concentration. After a one-day culture, the HepG2 cells supplied with DCP ceramic particles and were observed by microscopy. The observation results indicated that the ceramic particles were absorbed by the cells; moreover, the cells surrounded by the ceramic particles were ready to divide and grow, the cells which did not contact the ceramic particles still grew and divided as did the cells in the control sets. The results demonstrated that the ceramic particles have an affinity to the HepG2 cells, and the ceramic particles do not affect cell growth. The cells were stained with trypen blue and observed under microscopy lighted with a cool light 3 days later. The observed results indicated that the cells not only grew on the surfaces of the ceramic particles, some even covered whole ceramic particles (referring to FIG. 5). As shown in FIG. 5, the blue regions are HepG2 cells and the white reflecting regions are ceramic particles. This test demonstrates that there is a good affinity between the HepG2 cells and the ceramic particles.

In Vivo Treatment of Animal Hepatoma With Radioactive Ceramic Particles

Figure 6:
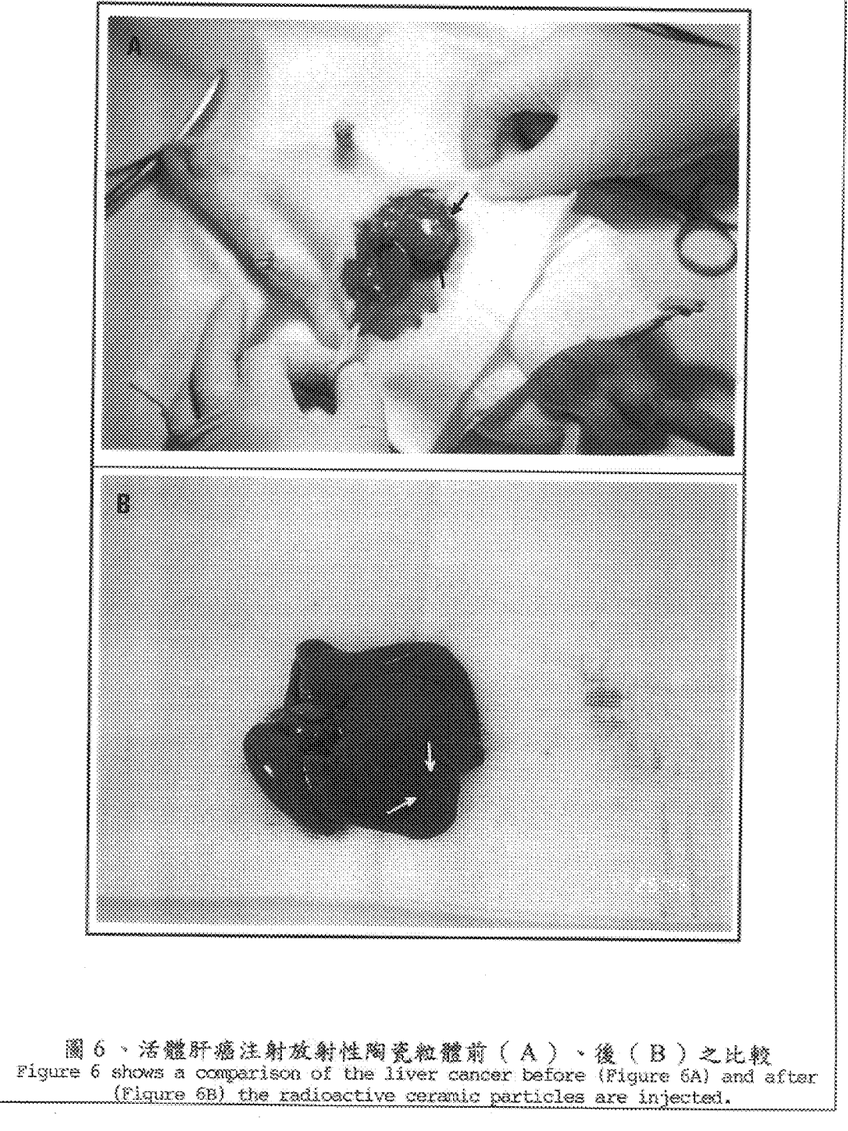

First, Sprague-Dawley mice of 250~300 g were anesthetized by i.p. injection with Ketamine (0.3 ml/100 g weight) and an incision was made along the central line of the abdomen. Second, the exposed liver was injected directly with 0.1~0.2 ml of N1S1 cells by a No.25 needle, and pressed with a cotton-label to stop bleeding. Then the muscular layer of the abdomen was sutured with catgut after the bleeding was stopped, and the skin layer was sutured by a wound needle. The localized hepatoma can be produced by means of the process described above. After 7~10 days, the abdomens of the mice were opened by means of the process described above to observe the growth of the N1S1 tumor (Referring to FIG. 6A).

After the tumor was formed, the mixed medium consisting of radioactive ceramic (glass) particles and iodized oil was injected directly into the N1S1 tumor to make the radioactive particles accumulate at the tumor site by the accumulation characteristics of weight iodized oil. For example, when the suspension medium consisting of DCP ceramic particles with sizes ranging from 35 to 50 $\mu$m and iodized oil was injected into the tumor site, the radioactive particles primarily distributed in the injection site of the tumor one hour later and there was no detectable radioactive activity found at any other site of the normal liver tissue. Three days after injection, the distribution of DCP injected into the hepatoma site was similar to that of one hour after injection. Some mice were sacrificed 16 days after injection to observe the growth of hepatoma injected with radioactive ceramic particles. The observations indicated that the size of the hepatoma was significantly reduced by 16 days after injection, and part of the hepatoma sites had even formed scar tissue. Some mice were sacrificed 90 days after injection to observe the growth of the hepatoma injected with radioactive ceramic particles, and the observation indicated that only scar tissue was left in the hepatoma sites (referring to FIG. 6B).

According to this invention, the spherical ceramic particles can be produced from ultra-pure materials and manufactured by granulation or spray pyrolysis methods. The yielded ceramic or glass particles can be selected and sorted by means of a suitable mesh and irradiated with an approximate flux of neutrons for a period of time to produced radioactive ceramic or glass particles with the same size. Subsequently, ceramic or glass particles with pure $\beta$-particle-emitting radionuclides can be produced after cooling. A suitable injection medium for localized treatment can be obtained by mixing a pharmacologically acceptable solvent serving as a suspension with the radioactive particles obtained according to above process. Then the radioactive ceramic or glass particles can be injected into the tumor or cancer sites of the patient, or directly implanted into the tumor or cancer site by operation. The injected or implanted radioactive particles can release $\beta$-particles with high energy that specifically kill the tumor or cancer cells, and do no damage to the adjacent normal cells. The present radiotherapy solves the drawbacks present in traditional radiotherapy or chemotherapy, wherein normal cells are also damaged by high dosage radiation.

From the above description, one skilled in this art can easily ascertain the essential characteristics of the present invention, and, without departing from the spirit and scope thereof, can make various changes and modifications of the invention to adapt it to various usage and conditions. Thus, other embodiments also fall within the scope of the following claims.

What is claimed:

1. A beta-emitting radioactive phosphate ceramic or phosphate glass particle, comprising bio-compatible crystalline calcium phosphate wherein the particle has a high efficiency of neutron activation with an appropriate half-life, and enough radiation strength to kill the tumor or cancer.

2. The radioactive particle as claimed in claim 1, wherein the size of the particle ranges from the level of $\mu$m to mm.

3. The radioactive particle as claimed in claim 1 wherein the particle is a mixture of calcium phosphate and hydroxyapatite.

4. The radioactive particle as claimed in claim 3, wherein the calcium phosphate particle is selected from the group consisting of dicalcium phosphate, tricalcium phosphate, calcium phosphate containing 33 parts by weight of calcium oxide (CaO-33), and calcium phosphate containing 47 parts by weight of calcium oxide (CaO-47).

5. The radioactive particles as claimed in claim 4, wherein the Cao-33 is an eutectic calcium phosphate consisting of $CaHPO_4.2H_2O$ and $Ca(H_2PO_4)_2.H_2O$ in a weight ratio of 1:2, and 33 parts by weight of CaO.

6. The radioactive particles as claimed in claim 4, wherein the CaO-47 is an eutectic calcium phosphate composed of $CaHPO_4.2H_2O$ and $CaCO_3$ in a weight ratio of 14:1, and 47 parts by weight of CaO.

7. The radioactive particle as claimed in claims 3, 4, 5, or 6, wherein the atomic ratio of calcium/phosphous in the calcium phosphate is about 2~0.5.

8. The radioactive particle as claimed in claims 3, 4, 5, or 6, wherein the atomic ratio of calcium/phosphous in the calcium phosphate is about 1.8~0.6.

9. The radioactive particle as claimed in claim 1, wherein the half-life of the radioactive particles is between 2 weeks and 4 weeks.

10. The radioactive particle as claimed in claim 1 wherein the particle is suspended in a contrast medium to form an injection medium which is directly injected into the tumor or cancer sites of the patient for local radiotherapy.

11. The radioactive particle as claimed in claim 10, wherein the size of the radioactive particle is between 20 $\mu$m and 70 $\mu$m.

12. The radioactive particle as claimed in claim 10, wherein the size of the particle is between 30 $\mu$m and 40 $\mu$m.

13. The radioactive particle as claimed in claim 11, wherein the contrast medium is an iodinated ester of popyl seed oil.

14. The radioactive particle as claimed in claim 1 wherein the particle is directly implanted into the tumor or cancer sites of the patient by surgical operation.

15. The radioactive particle as claimed in claim 14, wherein the size of the particle is between 0.1 m and 10 mm.

16. The radioactive particle as claimed in claim 14, wherein the size of the particle is between 0.5 mm and 5 mm.

17. The radioactive particle as claimed in claim 14, wherein the size of the particle is between 40 $\mu$m and 10 mm.

18. The radioactive particle as claimed in claim 17, wherein the size of the particle is between 100 $\mu$m and 5 mm.

* * * * *